United States Patent
Courtney et al.

(10) Patent No.: US 10,853,698 B2
(45) Date of Patent: Dec. 1, 2020

(54) SYSTEM AND METHOD OF USING MULTI-FRAME IMAGE FEATURES FOR OBJECT DETECTION

(71) Applicant: Konica Minolta Laboratory U.S.A., Inc., San Mateo, CA (US)

(72) Inventors: Logan Courtney, Oswego, IL (US); Haisong Gu, San Mateo, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

(21) Appl. No.: 16/347,237

(22) PCT Filed: Oct. 27, 2017

(86) PCT No.: PCT/US2017/058735
§ 371 (c)(1),
(2) Date: May 3, 2019

(87) PCT Pub. No.: WO2018/089210
PCT Pub. Date: May 17, 2018

(65) Prior Publication Data

US 2019/0332889 A1 Oct. 31, 2019

Related U.S. Application Data

(60) Provisional application No. 62/419,548, filed on Nov. 9, 2016.

(51) Int. Cl.
*G06K 9/62* (2006.01)
*G06K 9/00* (2006.01)
(Continued)

(52) U.S. Cl.
CPC ......... *G06K 9/627* (2013.01); *G06K 9/00744* (2013.01); *G06K 9/4671* (2013.01); *G06N 3/04* (2013.01)

(58) Field of Classification Search
CPC .. G06K 9/627; G06K 9/00744; G06K 9/4671; G06K 9/4628; G06K 9/3233;
(Continued)

(56) References Cited

U.S. PATENT DOCUMENTS 9,858,496 B2 * 1/2018 Sun ..................... G06K 9/3233
10,474,930 B1 * 11/2019 Kim ........................ G06N 3/04
(Continued)

OTHER PUBLICATIONS

Chiang, AT., et al., "Human Detection in Fish-Eye Images Using Hog-Based Detectors Over Rotated Windows," Department of Electrical and Computer Engineering, Game Innovation Lab, Polytechnic Institute of NYU, Brooklyn, NY 11201, USA, pp. 1-6, (Sep. 2014).
(Continued)

*Primary Examiner* — Michael S Osinski
(74) *Attorney, Agent, or Firm* — Buchanan Ingersoll & Rooney PC

(57) ABSTRACT

A method, a system, and a computer readable recording medium are disclosed for performing object recognition. The method includes receiving image data from an image; performing a multilayer feature extraction on the image data; generating current feature maps from the multilayer feature extraction; generating a region of proposal network map from at least the current feature maps, the region of proposal network map having one or more regions of interest; inputting previously generated feature maps and the current feature maps into a classifier with the region of proposed network map; and classifying the one or more regions of interest in the region of proposal network map.

20 Claims, 5 Drawing Sheets

(51) Int. Cl.
*G06K 9/46* (2006.01)
*G06N 3/04* (2006.01)

(58) Field of Classification Search
CPC ............ G06K 9/00805; G06K 9/6232; G06K 9/6262; G06K 9/6267; G06K 9/6274; G06K 9/6228; G06K 9/6273; G06N 3/04; G06N 3/08; G06N 3/0454; G06N 3/084; G06N 20/10; G06T 2207/20084; G06T 2207/20081; G06T 2207/10016; G06T 2210/12; G06T 3/4046; G06T 7/11
See application file for complete search history.

(56) References Cited

U.S. PATENT DOCUMENTS

| | | | | |
|---|---|---|---|---|
| 10,489,684 | B2* | 11/2019 | Choi | G06K 9/3241 |
| 10,509,987 | B1* | 12/2019 | Kim | G06K 9/627 |
| 10,636,164 | B2* | 4/2020 | Li | G06T 7/11 |
| 2012/0269384 | A1 | 10/2012 | Jones | G06K 9/00201 382/103 |
| 2015/0213302 | A1 | 7/2015 | Madabhushi et al. | |
| 2016/0104058 | A1 | 4/2016 | He et al. | |
| 2016/0358337 | A1* | 12/2016 | Dai | G06T 7/11 |
| 2017/0169315 | A1* | 6/2017 | Vaca Castano | G06K 9/6814 |
| 2017/0206426 | A1* | 7/2017 | Schrier | G06K 9/6273 |
| 2017/0358086 | A1* | 12/2017 | Dinu | G06K 9/4628 |
| 2018/0068198 | A1* | 3/2018 | Savvides | G06K 9/00228 |
| 2018/0096457 | A1* | 4/2018 | Savvides | G06K 9/6267 |
| 2018/0342061 | A1* | 11/2018 | Xiang | G06N 5/046 |
| 2019/0034800 | A1* | 1/2019 | Shiratani | G06T 7/0012 |
| 2019/0164290 | A1* | 5/2019 | Wang | G06K 9/4628 |
| 2019/0279014 | A1* | 9/2019 | Fang | G06K 9/4671 |
| 2020/0026956 | A1* | 1/2020 | Kumar | G06K 9/627 |
| 2020/0034976 | A1* | 1/2020 | Stone | G06T 7/246 |
| 2020/0057935 | A1* | 2/2020 | Wang | G06N 3/0472 |
| 2020/0074216 | A1* | 3/2020 | Zheng | G06K 9/4671 |
| 2020/0118423 | A1* | 4/2020 | Moura | G06N 3/08 |
| 2020/0143205 | A1* | 5/2020 | Yao | G06K 9/6262 |
| 2020/0210688 | A1* | 7/2020 | Xu | G06K 9/00281 |

OTHER PUBLICATIONS

Fan, J., et al., "Human Tracking Using Conventional Neural Networks," IEEE Transactions on Neural Networks, vol. 21, No. 10, p. 1610-1623 (Oct. 2010).
Girshick, R., et al., "Fast R-CNN," Computer Vision and Pattern Recognition arXiv:1506.01497v3 Publication online, https://arxiv.org/pdf/1504.08083.pdf, pp. 1-9, (Sep. 27, 2015).
Han, W., et al., "Seq-NMS for Video Object Detection," arXiv:1602.08465v2 [cs.CV], pp. 1-9, (Feb. 29, 2016).
Held, D., et al., "Learning to Track at 10 FPS with Deep Regression Networks," Computer Science Department, Stanford University, arXiv:1604.01802v1 [cs.CV], pp. 1-25, (Apr. 6, 2016).
International Search Report and Written Opinion issued in corresponding International Patent Application No. PCT/PCT/US2017/058735, 8 pages (dated Dec. 26, 2018).
Kang, K., et al., "T-CNN: Tubelets with Convolutional Neural Networks for Object Detection from Videos," arXiv:1604.02532v2 [cs.CV], pp. 1-9, (May 19, 2016).
Nam, H., et al., "Learning Multi-Domain Convolutional Neural Networks for Visual Tracking," Dept. of Computer Science and Engineering, POSTECH, Korea, arXiv:1510.07945v2 [cs.CV], pp. 1-10, (Jan. 6, 2016).
Ren, S., et al., "Faster R-CNN: Towards Real-Time Object Detection with Region Proposal Networks," Computer Vision and Pattern Recognition arXiv:1506.01497v3 Publication online, https://arxiv.org/abs/1506.01497, pp. 1-14, (Jan. 2016).
Tripathi, S., et al., "Refining Video Object Detection With Rnn: Context Matters: Refining Object Detection in Video with Recurrent Neural Networks," arXiv:1607.04648v2 [cs.CV], pp. 1-12, (Jul. 19, 2016).
Girshick, et al.: "Rich feature hierarchies for accurate object detection and semantic segmentation," IEEE Conference on Computer Vision and Pattern Recognition (CVPR), 2014 (8 pages).
Girshick, et al.: "Rich feature hierarchies for accurate object detection and semantic segmentation Tech report (v5)," http://www.cs.berkeley.edu/-rbg/rcnn, Oct. 22, 2014 (21 pages).

* cited by examiner

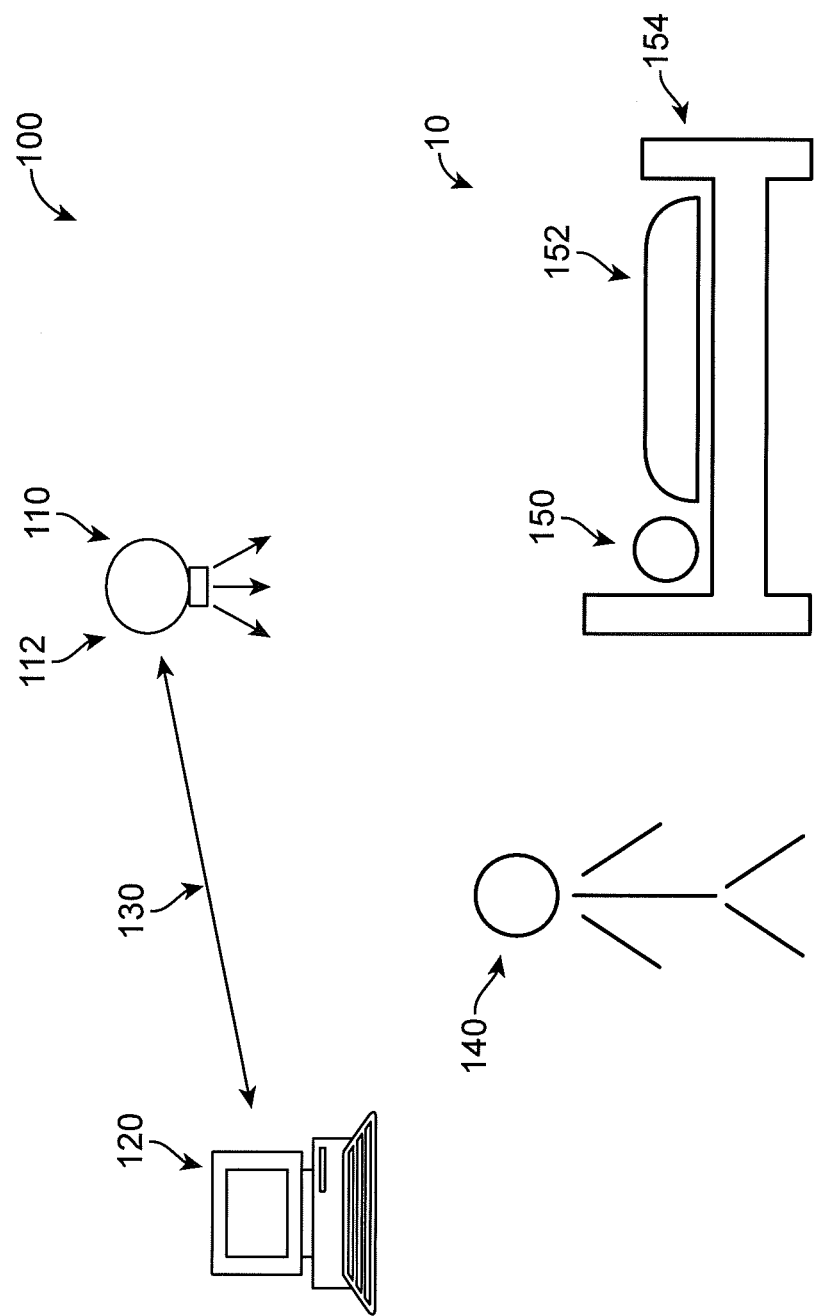

SYSTEM AND METHOD OF USING MULTI-FRAME IMAGE FEATURES FOR OBJECT DETECTION

CROSS-REFERENCES TO RELATED APPLICATIONS

This application claims priority to U.S. Provisional Application No. 62/419,548 filed on Nov. 9, 2016, the entire content of which is incorporated herein by reference.

FIELD OF THE INVENTION

The present disclosure relates to a system and method of using multi-frame image features for object detection or object recognition, and more particularly, to a system and method of using multi-frame image features, for example, using a convolutional neural network (CNN) with temporal information for real time detection of human(s) or other objects.

BACKGROUND OF THE INVENTION

Many computer systems and machines rely on person recognition techniques for various different applications. For example, in some applications, machines and computer systems, there may be a need to know if there is an object, for example, a human present at a particular location in order, for example, to turn on/off or activate a particular program. These programs can be used for security and safety issues, including, for example, monitoring of public areas, and individuals in, for example, prisons and/or senior living or nursing homes.

Object recognition using a layer-based classification/object detection system, for example, a convolution neural network (CNN) is known and can differentiate between classes of objects. The layer-based classification uses a segmented depth image to identify and differentiate between two or more objects within an image. However, one common error present in the layer-based classification system is classifying an object due to the detail as shown in the image, or alternatively, if the object is at an off angle (for example, 45 degrees), the object may appear distorted or curved in the depth image.

One solution that has been developed to improve object recognition is to use a deep convolutional neural network to classify objects and/or images. The deep convolutional neural network can use, for example, RGB images to classify objects and/or images. While recent improvements to the deep convolutional neural network have shown success at large object image recognition as well as increasing the size of the training set and tolerance of noise, the deep convolutional neural network is reliant on a single sending modality (for example, RGB image data). Not only is segmenting in RGB much more difficult and computationally expensive, but the classifier itself emphasizes learning a decision boundary based on edges and textures, features that may not be the only, or even the best, choice depending on the sensing modality and the object being recognized.

In general, a convolutional neural network (CNN) is a type of feed-forward artificial neural network in which the connectivity pattern between its neurons is inspired by the organization of the animal visual cortex, whose individual neurons are arranged in such a way that they respond to overlapping regions tiling the visual field. Convolutional networks were originally inspired by biological processes and are variations of multilayer perceptrons designed to use minimal amounts of preprocessing.

When used for image recognition, convolutional neural networks (CNNs) can consist of multiple layers of small neuron collections, which process portions of the input image, called receptive fields. The outputs of these collections are then tiled so that their input regions overlap, to obtain a better representation of the original image, which can be repeated for each layer.

SUMMARY OF THE INVENTION

In consideration of the above issues, it would be desirable to have a system and method of using multi-frame image features for detecting objects, and more particularly, to a system and method of using multi-frame image features, for example, using a convolutional neural network (CNN) with temporal information for real time detection of human(s) or other objections.

A method is disclosed for object recognition on an image of a time series of images, the method comprising: receiving image data from the image; performing a multilayer feature extraction on the image data; generating current feature maps from the multilayer feature extraction; generating a region of proposal network map from at least the current feature maps, the region of proposal network map having one or more regions of interest; inputting previously generated feature maps and the current feature maps into a classifier with the region of proposed network map, the previously generated feature maps generated from at least one previous image of the time series of images; and classifying the one or more regions of interest in the region of proposal network map.

A system is disclosed for object recognition on an image of a time series of images, the system comprising: a processor; and a memory storing instructions that, when executed, cause the system to: receive image data from the image; perform a multilayer feature extraction on the image data; generate current feature maps from the multilayer feature extraction; generate a region of proposal network map from at least the current feature maps, the region of proposal network map having one or more regions of interest; input previously generated feature maps and the current feature maps into a classifier with the region of proposed network map, the previously generated feature maps generated from at least one previous image of the time series of images; and classify the one or more regions of interest in the region of proposal network map.

A non-transitory computer readable recording medium stored with a computer readable program code for performing object recognition on an image of a time series of images is disclosed, the computer readable program code configured to execute a process comprising: receiving image data from the image; performing a multilayer feature extraction on the image data; generating current feature maps from the multilayer feature extraction; generating a region of proposal network map from at least the current feature maps, the region of proposal network map having one or more regions of interest; inputting previously generated feature maps and the current feature maps into a classifier with the region of proposed network map, the previously generated feature maps generated from at least one previous image of the time series of images; and classifying the one or more regions of interest in the region of proposal network map.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is an illustration of a system of using multi-frame image features, for example, using a convolutional neural network (CNN) with temporal information for real time detection of human(s) or other objections.

DETAILED DESCRIPTION

Figure 2A:
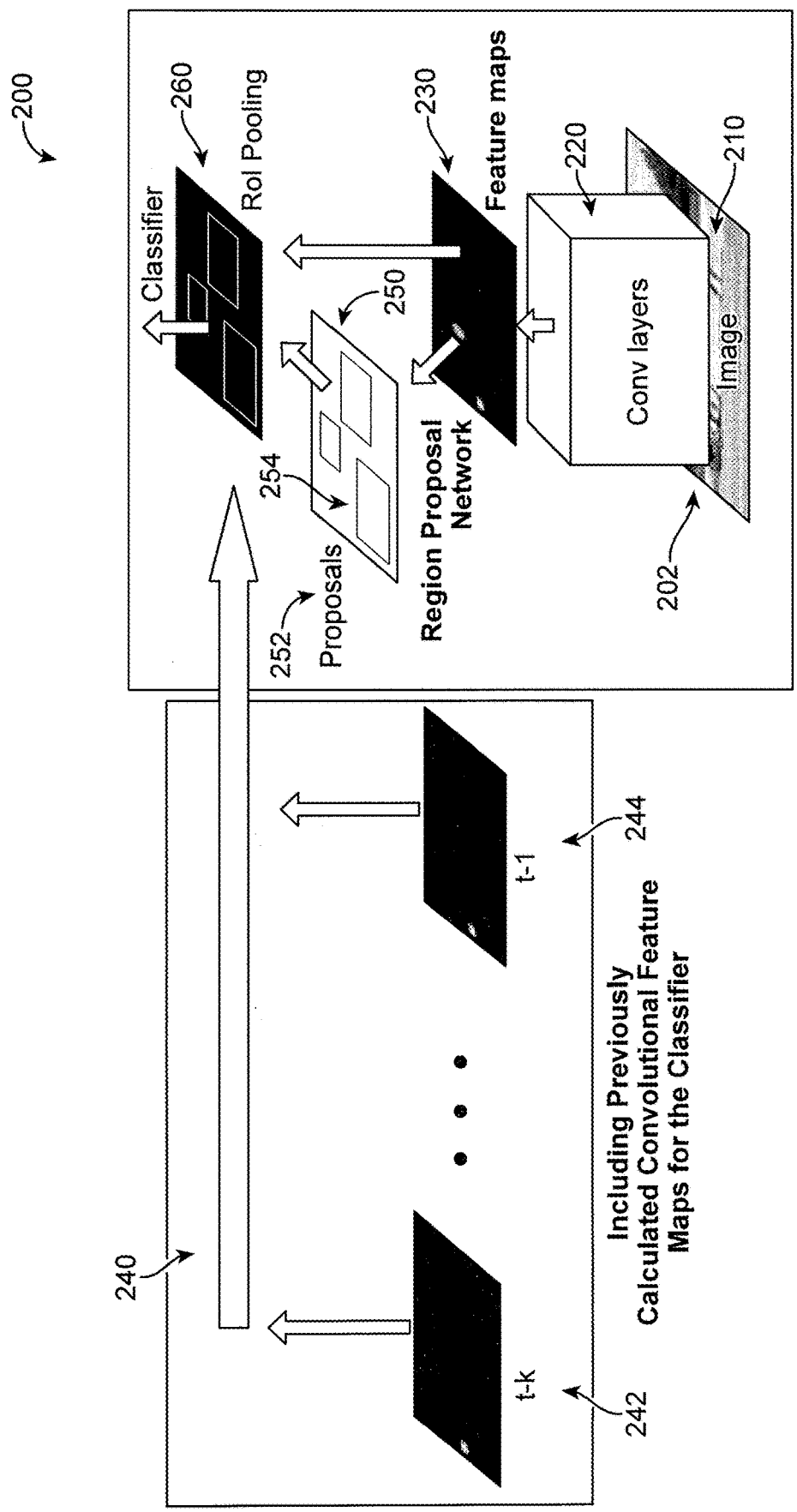
FIG. 2A is an illustration of a system and method of using multi-frame image features for detecting objects in accordance with an exemplary embodiment.

Reference will now be made in detail to the present preferred embodiments of the invention, examples of which are illustrated in the accompanying drawings. Wherever possible, the same reference numbers are used in the drawings and the description to refer to the same or like parts.

In accordance with an exemplary embodiment, it would be desirable to have a system and method of using multi-frame image features for detecting objects, and more particularly, to a system and method of using multi-frame image features, for example, using a convolutional neural network (CNN) with temporal information to detect human(s) or other objections in real time.

FIG. 1 illustrates an example of a system 100 of using multi-frame image features, for example, using a convolutional neural network (CNN) with temporal information to detect human(s) 140, 150 or other objects 152, 154 (for example, a blanket 152) and a bed/furniture 154) in an image 10 in accordance with an exemplary embodiment. For example, the system 100 can advantageously recognize objects 140, 150, 152, 154 (for example, people 140, 150) in depth images even when important aspects of those objects, for example, a portion of a person's body, head, or shoulders can be occluded or blocked from view of a detection device or sensor 110, for example, from the detection device or sensor's perspective 110. The occlusions may be caused by, but are not limited to, for example, physical objects 152 in the frame that block part of the person 150 from view, for example, a blanket 152 on an individual sleeping 150, the edge of the detection device image plane, and other artifacts that may block or obscure objects in images from being visible, such as lighting, focus, and noise, during image capture.

As shown in FIG. 1, in accordance with an exemplary embodiment, the system 100 can include the detection system or sensor 110, preferably, for example, in the form of a camera 112, a computer system or processing unit 120, and a network connection 130. In accordance with an exemplary embodiment, the detection system or sensor 110 can be configured to perform all activity recognition on its own embedded hardware and transfers all necessary information such as video stream and recognized activity to the computer system or processing unit 120. The computer system or processing unit 120 is configured to analyze and process data received from the detection system or sensor 110. For example, in accordance with an exemplary embodiment, the detection system or sensor 110 communicates with the computer system or processing unit 120 via a network connection 130.

In accordance with an exemplary embodiment, the detection system or sensor 110 can include, for example, one or more sensors configured to capture light and other signals from the surrounding environment and to generate and/or process sensor data, such as depth data, therefrom. For example, in accordance with an exemplary embodiment, the detection device or sensor 110 can be, for example, an infrared omnidirectional or fisheye camera 112. Alternatively, the detection device or sensor 110 can be, for example, a range camera, such as but not limited to an RGB-D camera, a stereo camera, a structured light camera/scanner, a time-of-flight camera, an interferometer, a modulation imager, a laser rangefinder, a light-field camera, or an intensified charge-coupled device (CCD) camera.

In addition, the detection device or sensor 110 can be other types of sensors, such as but not limited to an ultrasound sensor or a color sensor. In some embodiments, the sensor and/or detection system 110 may include a combination of different types of sensors, such as accelerometers, gyroscopes, thermometers, barometers, thermocouples, or other conventional sensing devices. In accordance with an exemplary embodiment, the sensor and/or detection system 110 can be incorporated into the computer system or processing unit 120, or may be a separate device as shown in FIG. 1, and coupled to the computer system or processing unit 120 via the network connection 130, for example a wireless or wired connection.

The computer system or processing unit 120 can include a processor or central processing unit (CPU) and one or more memories for storing software programs and data. The processor or CPU carries out the instructions of a computer program, which operates and/or controls at least a portion of the functionality of the computer system or processing unit 120. The computer system or processing unit 120 can also include an input unit, a display unit or graphical user interface (GUI), and a network interface (I/F), which is connected to the network communication (or network) 130. The computer system or processing unit 120 can also include an operating system (OS), which manages the computer hardware and provides common services for efficient execution of various software programs. For example, some embodiments may include additional or fewer computer system or processing unit 120, services, and/or networks, and may implement various functionality locally or remotely on other computing devices 120. Further, various entities may be integrated into to a single computing system or processing unit 120 or distributed across additional computing devices or systems 120.

In accordance with an exemplary embodiment, the communication network 130 may include a conventional type network, wired or wireless, and may have any number of configurations, such as a star configuration, token ring configuration, or other known configurations. The communication network 130 may include one or more local area networks ("LANs"), wide area networks ("WANs") (e.g., the Internet), virtual private networks ("VPNs"), peer-topeer networks, near-field networks (e.g., Bluetooth™), cellular networks (for example, 3G, 4G, other generations), and/or any other interconnected data path across which multiple computing nodes may communicate.

In accordance with an exemplary embodiment, data may be transmitted in encrypted or unencrypted form between the nodes of the communication network 130 using a variety of different communication protocols including, for example, various Internet layer, transport layer, or application layer protocols. For example, in accordance with an exemplary embodiment, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOW), file transfer protocol (FTP), WebSocket (WS), wireless access protocol (WAP), various messaging protocols (SMS, MMS, XMS, IMAP, SMTP, POP, WebDAV, etc.), and other known protocols.

In accordance with an exemplary embodiment as shown in FIG. 1, the detection device or sensor 110 can be a downward facing camera, for example, an infrared omnidirectional or fisheye camera 112 located in a room 10, for example, in a senior care facility or prison environment, in which the individual or people require continuous monitoring or at least occasional monitoring. However, in such environment, various objects like beds, desks, dressers, doors, curtains, windows, blankets 152 can be present, which also require processing. For example, grayscale images from an infrared camera 112, for example, having a pixel ratio of 1280×960 may lack fine detail one would see from an RGB image. In addition, using omnidirectional or fisheye cameras 112, the humans 140, 150 may appear in any orientation, for example, upside down or sideways. Accordingly, it would be desirable that calculations be performed in real-time, for example, greater than 5 (five) frames per second (>5 fps) to improve the detection results.

In addition, for example, single frame object detection with CNN may have difficulty without using temporal context due to extreme variations in pose, for example, sleeping, standing, sitting, and sitting in a wheelchair. For example, a person's full body may not always be viewable. Alternatively, when directly below the sensor 110 or the camera 112, the sensor 110 or camera 112 may only be able to see the top of the head, or when standing near the edge of the scene, the body may appear distorted. In addition, extreme variations in lighting, both very light and very dark, and videos contain multiple people, which can occlude one or more individuals in an image can all be problematic.

Accordingly, it would be desirable, to incorporate or use temporal information from previous images of a time serial of images, for example, image data or frames, as well as current image data and frame features to improve detection accuracy. Advantageously, the previous image data and frame information can allow for fewer false positives/missed detections as well as handling occlusion issues frequently seen during a video sequence with a moving object. In addition, as disclosed herein, the system and method can be configured to be capable of using the temporal information while still performing in real time (for example, greater than 5 (five) frames per second (fps)).

FIG. 2A is an illustration of a system 200 of using multi-frame image features for detecting objects in accordance with an exemplary embodiment. As shown in FIG. 2A, the system 200 obtains an image (or images) 202 from a detection device or sensor 110 (FIG. 1). In accordance with an exemplary embodiment, image data 210 from the image 202 is forwarded from the detection device or sensor 110 to the computing system or processing unit 120 for processing as disclosed herein.

In accordance with an exemplary embodiment, the image data 210 is passed through a series of image convolutions (or a multilayer feature extraction) 220 with learned weights to produce convolutional maps of high-level image features (or feature maps), which describe in an abstract nature what is shown or present in the image 202, rather than specifically identify or classifying the features, for example, as a specific object. The convolutional maps (or feature maps) 230 can be used to produce a region proposal network (RPN) 250, which includes one or more regions of interest (ROI) or region proposals 252, and wherein each region of interest 252 can have an object score and bounding box coordinates 254 via a fully connected neural network. In accordance with an exemplary embodiment, the object score, for example, can be a "probability" of the bounding box 252 containing an object 140, 150, 152, 154, for example, a person 140 of interest within the image 202.

In accordance with an exemplary embodiment, the RPN map 250 can then be used with at least the previously calculated convolutional maps (or feature maps) 240, 242, 244 of the image 202 obtained prior to the current feature maps 230. In accordance with an exemplary embodiment, the previously calculated convolutional maps (or features maps) 240, 242, 244 are generated from at least one previous (or past) image of the time series of images. For example, feature maps t-k 242 through feature maps t-1 244 can be used to calculate a class score, for example, does the bounding box coordinates 254 contain the full body of a human or any other particular object of interest. In addition, the bounding box coordinates 254 can be regresses to a more accurate location via another fully connected neural network or classification network (or classifier) 260.

In accordance with an exemplary embodiment, the convolutional maps (or feature maps) 240 from previous images of the time series of images can be saved, for example, in a memory of the computer system or processing unit 120, after each calculation to be used as an additional input, for example, to the region proposal network (RPN) 250, or the classification network 260. Thus, in accordance with an exemplary embodiment, temporal information stored as previously generates feature maps 240, 242, 244 can be incorporated into the detected probability as opposed to only using a single (or current) image frame feature 230.

In accordance with an exemplary embodiment, generating the feature maps 230 from the multi-frame image or convolutional layers 220 for an image 202 is the bulk of the computation (for example, greater than 95%). In accordance with the system 200 as disclosed herein, this calculation is only performed once for the image data 210 for each image 202 and the calculation is temporarily stored for use in subsequent calculations allowing the method and system 200 to operate in real time. Advantageously, for example, the system 200 can be used for detection and/or tracking of humans 140, 150, for example, in image sequences (around 5 frames per second) with a relatively high detection rate, a relatively low false positive rate, and a relatively high degree of overlap between predicted bounding boxes and true bounding boxes 254.

In accordance with an exemplary embodiment, the system 200 as disclosed herein can be configured to use only previous inputs, or features maps 240, 242, rather than previous outputs, or classified images 260. In addition, the use of only the previous inputs or features maps 240 allows the system and method 200 to be more robust or capable of correcting errors in previous frames. In accordance with an exemplary embodiment, the saved convolutional feature maps 240, 242, 244 from previous images can be used to improve the prediction results for a current image 210. For example, in accordance with an exemplary embodiment, the method 200 as disclosed herein comprises a fully trainable method for including temporal information within a RPN/classification network such as but not limited to Faster-RCNN (Region-based Convolutional Neural Networks).

Figure 2B:
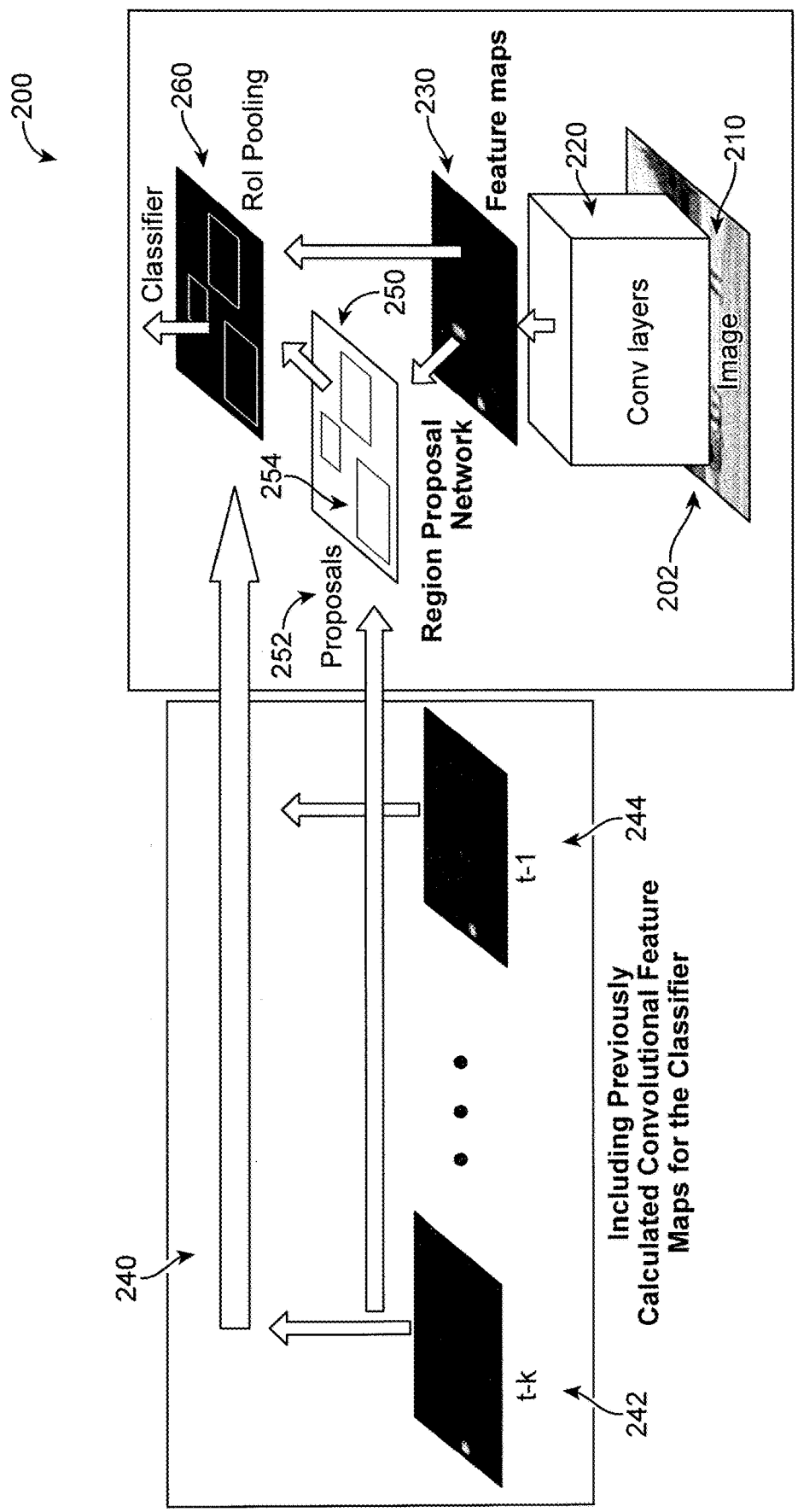
FIG. 2B is an illustration of a system and method of using multi-frame image features for detecting objects in accordance with another exemplary embodiment.

In accordance with an exemplary embodiment, a two-part training process is disclosed, which includes, for example, training a regular Faster-RCNN model on single images 210, and the learned weights for calculating the convolutional feature maps 240, 242, 244 are saved. The convolutional feature maps 240, 242, 244 from each of the images 202 are extracted, and the convolutional layers' weights are frozen during training. In accordance with an exemplary embodiment, the previous frame's convolutional maps 240, 242, 244 can be used in addition to the current frame's convolutional maps 230 to train both the RPN 250 and classification network 260 as shown in FIG. 2B, or alternatively, just the classification network 260 alone as shown in FIG. 2A.

In accordance with an exemplary embodiment, for example, the true labels (for example, classification results for classifying an object) from the previous frames (not shown) are therefore not used, and instead, the method and system uses only the learned convolutional maps (or feature maps) 230, 240, 242, 244. Thus, in accordance with an exemplary embodiment, the system (or network) 200 can learn what features to focus on between frames as opposed to instructed (or told) what to focus on via a true label in which objects are feed to the classifier. Thus, the system 200 can be more robust to detection and classification errors from previous frames, since full convolutional features maps 230 are used as an input rather than results from the classification.

In accordance with an exemplary embodiment, the current feature maps can be stored in a memory of the detection device or sensor 110, or the computer system or processing unit 120 with the previously generated feature maps for a predetermined time frame. After the predetermined time frame, the previously generated feature maps are preferably deleted so that additional feature maps can be stored. For example, in accordance with an exemplary embodiment, the deletion of the previously generated feature maps can be on a first in, first out (FIFO) basis, or any other known manipulation method.

In addition, most tracking networks trained on image pairs use the known location of the object in the previous image as an input to the network. The use of known locations of objects can improve tracking performance because smooth motions are assumed and the object in the subsequent frame is, therefore, correlated with the location of the object in the previous frame. However, this makes the first detection (before previous image information exists) essential for these networks to work appropriately. If the network is trained on true locations from the previous image, and during test time, there is an error in a previous frame for any reason, this can cause issues for tracking the object in each of the subsequent frames.

In accordance with an exemplary embodiment, as disclosed herein, the system 200 uses the convolutional feature maps (or feature maps) 240, 242, 244 already trained instead of the true object location, which provides that later networks are trained with exactly the same sort of features/inputs that the system 200 would see in a testing scenario. Thus, the system 200 allows the network to learn what features are important to track as opposed to being told exactly what to track.

In accordance with an exemplary embodiment, the classifier 260 can identify the objects in the depth image based on the set of layers. In some embodiments, the classifier 260 may compare the layers associated with each object to a set of stored object models to determine a match. For example, to determine a matching object model, the classifier 260 may compare the regions of interest using known classifiers. In accordance with an exemplary embodiment, the object models for the classification model may be input manually, for example, by a user or an administrator, and/or may be machine learned using various machine-learning algorithms.

In accordance with an exemplary embodiment, the system and method 200 as disclosed herein can be used for security, for example, for monitoring of prisoners, assisted living centers, and any location where, for example, tracking, recognition, or detection of human movement and/or actions is needed. In accordance with an exemplary, the results of the detection can be sent to the display unit or graphical user interface (GUI) of the computer system or processing unit 120, or an alarm, for example, in a room or place 10 being monitored can be sounded, a message can be sent to one or more client devices upon detection of an object, which has been classified to trigger an alarm or warning.

FIG. 2B is an illustration of a system and method of using multi-frame image features for detecting objects in accordance with another exemplary embodiment. As shown in FIG. 2B, the previous frame's convolutional maps 240, 242, 244 can be used in addition to the current frame's convolutional maps 230 to train both the RPN 250 and the classifier 260. In accordance with an exemplary embodiment, the region of proposal network (RPN) map 250 can be generated from both the previously generated feature maps 240, 242, 244 and the current feature maps 230.

Figure 3:
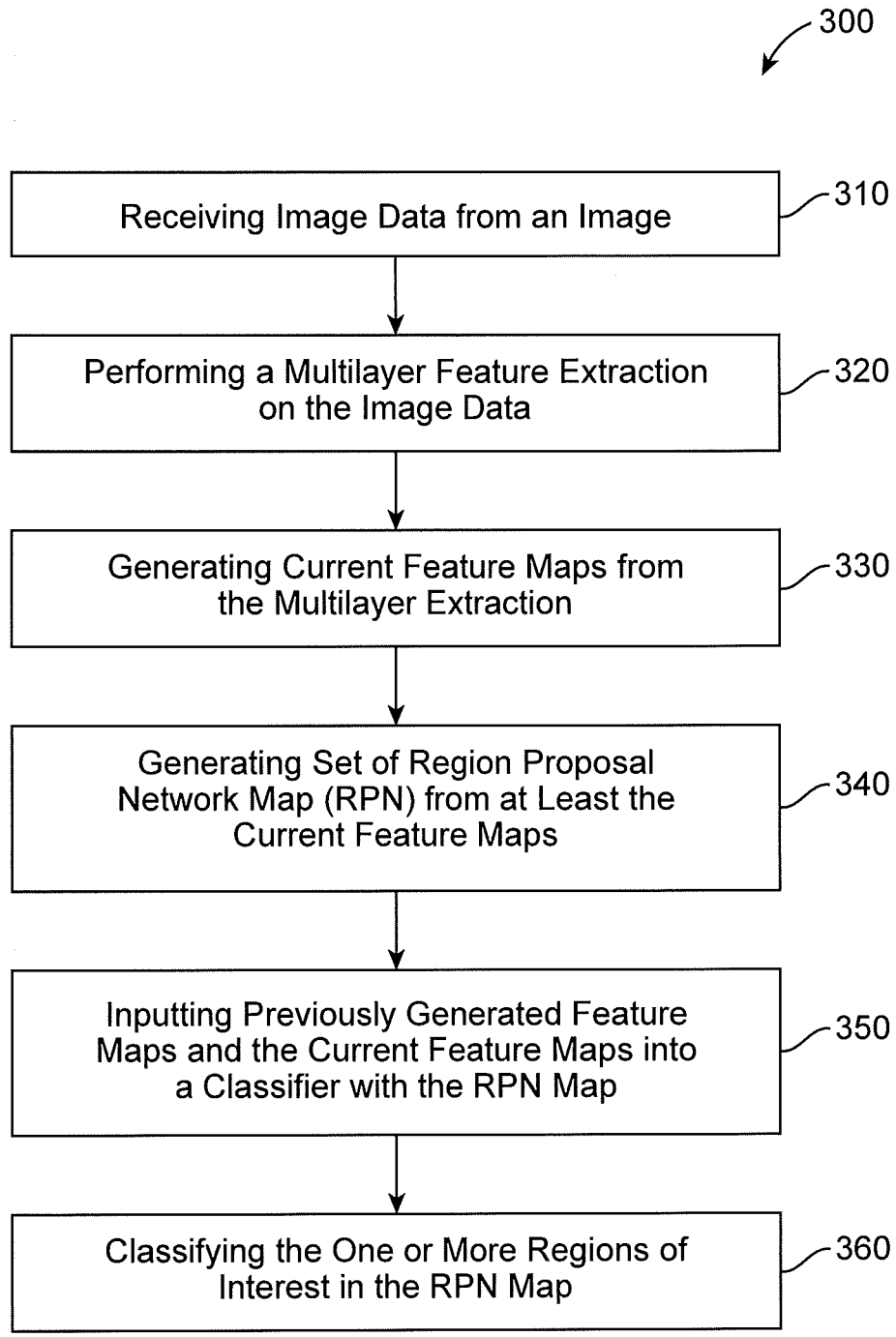
FIG. 3 is a flow chart showing the use of multi-frame image features for detecting objects in accordance with an exemplary embodiment.

FIG. 3 is a flow chart 300 showing the use of a multi-frame image features for detecting objects in accordance with an exemplary embodiment. As shown in FIG. 3, the process begins in step 310, when the computer system or processing unit 120 receives image data 210 from an image 202. As disclosed herein the image data 210 is preferably received from a detection device or sensor 110, preferably, for example, an omnidirectional or fisheye camera 112. In step 320, a multilayer feature extraction 220 is performed on the image data 210. The multilayer feature extraction can be, for example, a convolution neural network application. In step 330, the current feature maps 230 are generated from the multilayer feature extraction 220. In step 340, a region of proposal network (RPN) map 250 is generated from at least the current feature maps 230. In accordance with an exemplary embodiment, the region of proposal network map 250 preferably has one or more regions of interest 254. In step 350, previously generated feature maps 240, 242, 244, which have been generated from at least one previous or past image of the time series of images, and the current feature maps 230 are input into a classifier 260 with the region of proposed network map 250. In step 360, the one or more regions of interest 254 in the RPN map 250 are classified by the classifier 260.

Figure 4:
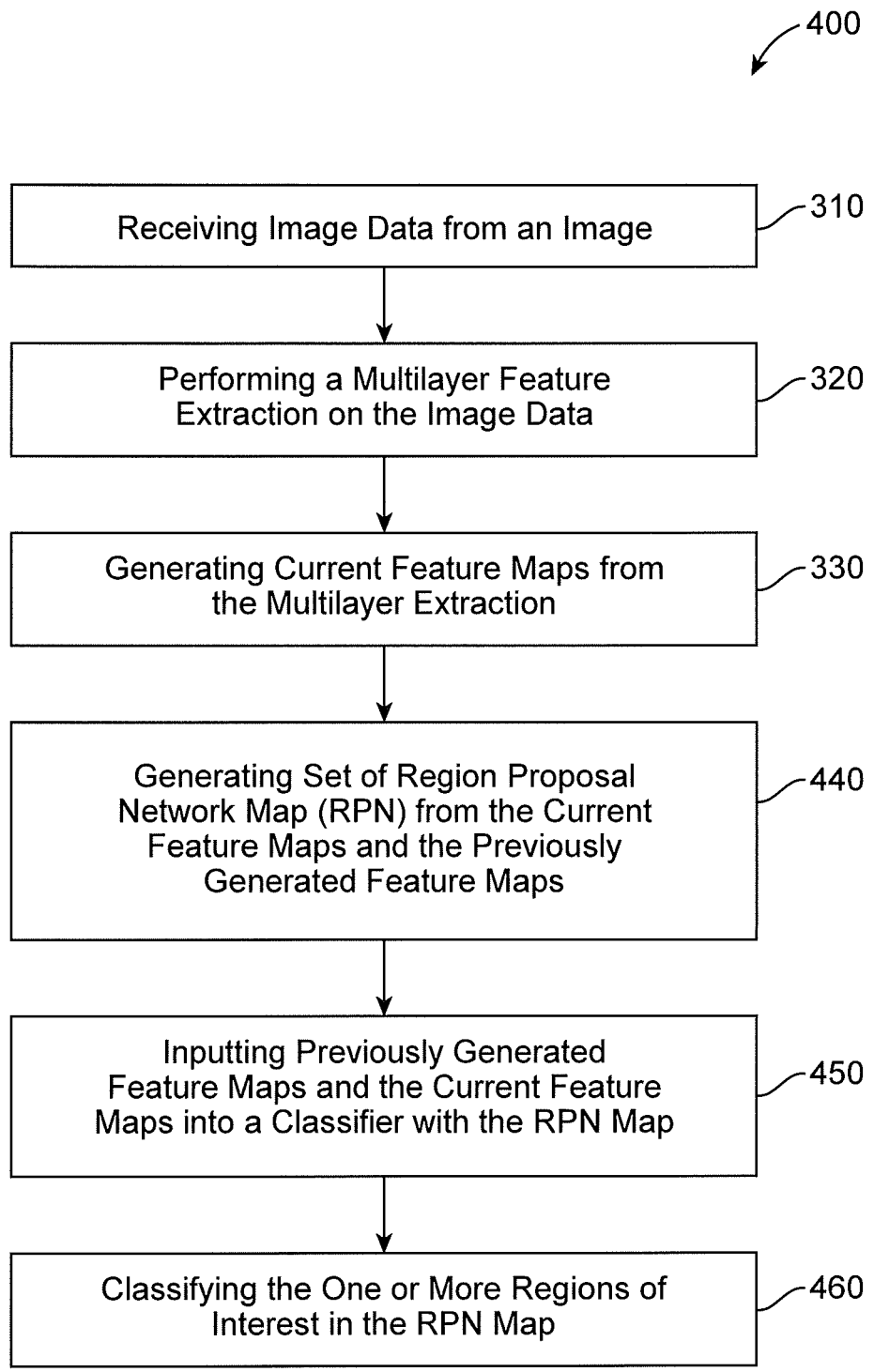
FIG. 4 is a flow chart showing the use of multi-frame image features for detecting objects in accordance with another exemplary embodiment.

FIG. 4 is a flow chart 400 showing the use of multi-frame image features for detecting objects in accordance with another exemplary embodiment. As shown in FIG. 4, steps 310, 320, and 330 are the same as in FIG. 3. After generating the current feature maps 230 from the multilayer extraction 220, in step 440, a region of proposal network map 250 is generated from the previously generated feature maps 240, 242, 244, which have been generated from at least one previous or past image of the time series of images, and the current feature maps 230. In step 450, the previously generated feature maps 240, 242, 244, and the current feature maps 230 are input into a classifier 260 with the RPN map 250. In step 460, the one or more regions of interest 254 in the RPN map 250 are classified by the classifier 260.

In accordance with an exemplary embodiment, a non-transitory computer readable recording medium stored with a computer readable program code for performing object recognition on an image of a time series of images is disclosed, the computer readable program code configured to execute a process comprising: receiving image data from the image; performing a multilayer feature extraction on the image data; generating current feature maps from the multilayer feature extraction; generating a region of proposal network map from at least the current feature maps, the region of proposal network map having one or more regions of interest; inputting previously generated feature maps and the current feature maps into a classifier with the region of proposed network map, the previously generated feature maps generated from at least one previous image of the time series of images; and classifying the one or more regions of interest in the region of proposal network map.

The non-transitory computer readable medium may be a magnetic recording medium, a magneto-optic recording medium, or any other recording medium which will be developed in future, all of which can be considered applicable to the present invention in all the same way. Duplicates of such medium including primary and secondary duplicate products and others are considered equivalent to the above medium without doubt. Furthermore, even if an embodiment of the present invention is a combination of software and hardware, it does not deviate from the concept of the invention at all. The present invention may be implemented such that its software part has been written onto a recording medium in advance and will be read as required in operation.

It will be apparent to those skilled in the art that various modifications and variation can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for object recognition on an image of a time series of images, the method comprising:
   receiving image data from the image;
   performing a multilayer feature extraction on the image data;
   generating current feature maps from the multilayer feature extraction;
   generating a region of proposal network map from at least the current feature maps, the region of proposal network map having one or more regions of interest;
   inputting previously generated feature maps and the current feature maps into a classifier with the region of proposed network map, the previously generated feature maps generated from at least one previous image of the time series of images; and
   classifying the one or more regions of interest in the region of proposal network map.

2. The method of claim 1, comprising:
   generating the region of proposal network map from the previously generated feature maps and the current feature maps.

3. The method of claim 1, comprising:
   generating the current feature maps by passing the image data through a series of image convolutions with learned weights, the current feature maps containing high-level image features of objects within the image data.

4. The method of claim 1, wherein the region of proposal network map comprises:
   an object score and bounding box coordinates for each of the one or more regions of interest, the object score based on a probability that the each of the one or more regions of interest contains an object.

5. The method of claim 4, comprising:
   calculating a class score using the region of proposal network map and previously generated feature maps, the class score relating to a probability that the bounding box coordinates contain an object of interest; and
   regressing the bounding box coordinates to a more accurate location via another feature map or classification if the bounding box coordinates do not include an entirety of the object of interest.

6. The method of claim 1, comprising:
   storing the current feature maps with the previously generated feature maps for a predetermined time frame; and
   deleting the previously generated feature maps after a predetermined time frame for each of the previously generated feature maps on a first in, first out basis.

7. The method of claim 1, comprising:
   generating the current feature maps and the previously generated feature maps with a convolutional neural network (CNN) algorithm.

8. The method of claim 1, comprising:
   obtaining the image data from an omnidirectional infrared camera; and
   monitoring at least one room, wherein the omnidirectional infrared camera can detect an entirety of the room.

9. The method of claim 1, comprising:
   obtaining at least 5 frames per second of image data from the omnidirectional camera such that the image data is in real-time.

10. A system for object recognition on an image of a time series of images, the system comprising:
    a processor; and
    a memory storing instructions that, when executed, cause the system to:
      receive image data from the image;
      perform a multilayer feature extraction on the image data;
      generate current feature maps from the multilayer feature extraction;
      generate a region of proposal network map from at least the current feature maps, the region of proposal network map having one or more regions of interest;
      input previously generated feature maps and the current feature maps into a classifier with the region of proposed network map, the previously generated feature maps generated from at least one previous image of the time series of images; and
      classify the one or more regions of interest in the region of proposal network map.

11. The system of claim 10, wherein the region of proposal network map is generated from the previously generated feature maps and the current feature maps.

12. The system of claim 10, wherein the current feature maps are generated by passing the image data through a series of image convolutions with learned weights, the current feature maps containing high-level image features of objects within the image data.

13. The system of claim 10, wherein the region of proposal network map includes an object score and bounding box coordinates for each of the one or more regions of interest, the object score based on a probability that that the each of the one or more regions of interest contains an object; and
- a class score is calculated using the region of proposal network map and previously generated feature maps, the class score relating to a probability that the bounding box coordinates contain an object of interest.

14. The system of claim 10, wherein the bounding box coordinates are regressed to a more accurate location via another feature map or classification if the bounding box coordinates do not include an entirety of the object of interest.

15. The system of claim 10, wherein the current feature maps and previously generated feature maps are generated with a convolutional neural network (CNN) algorithm.

16. The system of claim 10, comprising:
- an omnidirectional infrared camera configured to obtain the image.

17. A non-transitory computer readable recording medium stored with a computer readable program code for performing object recognition on an image of a time series of images, the computer readable program code configured to execute a process comprising:
- receiving image data from the image;
- performing a multilayer feature extraction on the image data;
- generating current feature maps from the multilayer feature extraction;
- generating a region of proposal network map from at least the current feature maps, the region of proposal network map having one or more regions of interest;
- inputting previously generated feature maps and the current feature maps into a classifier with the region of proposed network map, the previously generated feature maps generated from at least one previous image of the time series of images; and
- classifying the one or more regions of interest in the region of proposal network map.

18. The computer readable recording medium of claim 17, comprising:
- generating the region of proposal network map from the previously generated feature maps and the current feature maps.

19. The computer readable recording medium of claim 17, comprising:
- generating the current feature maps by passing the image data through a series of image convolutions with learned weights, the current feature maps containing high-level image features of objects within the image data.

20. The computer readable recording medium of claim 17, wherein the region of proposal network map comprises:
- an object score and bounding box coordinates for each of the one or more regions of interest, the object score based on a probability that the each of the one or more regions of interest contains an object, and the process further comprises:
- calculating a class score using the region of proposal network map and previously generated feature maps, the class score relating to a probability that the bounding box coordinates contain an object of interest; and
- regressing the bounding box coordinates to a more accurate location via another feature map or classification if the bounding box coordinates do not include an entirety of the object of interest.

* * * * *